United States Patent [19]
Friden

[11] 4,435,175
[45] Mar. 6, 1984

[54] INFUSION NEEDLE CARRIER

[76] Inventor: G. Burton Friden, 2200 Broad St., Colmar, Pa. 18915

[21] Appl. No.: 301,190

[22] Filed: Sep. 11, 1981

[51] Int. Cl.³ .............................................. A61M 5/00
[52] U.S. Cl. ................................... 604/177; 604/264; 128/DIG. 26
[58] Field of Search ............... 128/221, 214 R, 214.4, 128/347, DIG. 26, 215, 133; 24/255 SL, 255 BS, 255 A, 255 R, 254, 249 R, 262, 137, 263 R, 263 SB, 263 B, 67.3, 67.5, 67.7, 67.9, 67.11; 604/51, 52, 93, 158, 161, 164, 174, 177, 178, 264, 272

[56] References Cited
U.S. PATENT DOCUMENTS

| | | | |
|---|---|---|---|
| 2,402,306 | 6/1946 | Turkel | 128/214 R |
| 2,409,432 | 10/1946 | Hubbard | 128/214 R |
| 2,922,420 | 1/1960 | Cheng | 604/158 X |
| 3,538,915 | 11/1970 | Frampton et al. | 128/221 X |
| 3,640,275 | 2/1972 | Burke et al. | 128/214 R |
| 3,651,807 | 3/1972 | Huggins | 604/161 |
| 3,713,442 | 1/1972 | Walter | 128/221 X |
| 3,950,829 | 4/1976 | Cohen | 24/137 A X |
| 4,198,973 | 4/1980 | Millet | 128/214.4 |
| 4,209,015 | 6/1980 | Wicks | 128/DIG. 26 |
| 4,362,156 | 12/1982 | Feller, Jr. et al. | 604/177 X |

FOREIGN PATENT DOCUMENTS
1534122 7/1968 France ............................... 128/221

Primary Examiner—C. Fred Rosenbaum
Assistant Examiner—Michelle N. Lester
Attorney, Agent, or Firm—Paul Maleson

[57] ABSTRACT

A device for carrying, manipulating, and securing a hollow, medical subcutaneous infusion needle. The carrier comprises a body firmly holding the needle, a pair of laterally extending relatively angularly variable wings, and a control member. One handed-grasping and manipulation of the control member permits both unlocking the wings for changing their angular relationship to accommodate the desired angle of insertion of the needle into a patient, and locking the wings to brace the carrier at the desired angle. Manipulation of the control member also permits rotation of the needle independent of the angle of insertion, during the insertion procedure. Squeezing the control member provides an unset condition in which relative movement of the wings with respect to each other and with respect to the body may occur, and relaxation of squeezing provides a set or locked condition. The control member is repeatably manipulatable for purposes of readjusting the depth of penetration, angle of insertion, or rotational setting of the needle. Following desired placement of the needle, the control member may be freely swung to a substantially flat and out of the way position and the device secured to the patient.

21 Claims, 10 Drawing Figures

INFUSION NEEDLE CARRIER

BACKGROUND OF THE INVENTION

1. Field of the Invention

This invention relates to medical devices and more particularly relates to devices useful in the insertion and maintenance of subcutaneous needles in patients. More particularly, it relates to a device which carries an intravascular infusion needle, adapted to be connected to a source of liquid to be infused. It aids in the handling and reliable insertion of the needle, and also in the maintenance of the needle in its desired inserted condition. It is particularly useful, but not exclusively intended for pediatric use.

2. Prior Art

There have been many known prior expedients dealing with the same field. Many patents directed to the same field are found in U.S. Patent Class 128/214 seq. Some examples of earlier patents showing earlier expedients include U.S. Pat. Nos. 3,064,648; 3,538,915; 3,640,275; 2,409,432; and 2,402,306. These cited patents are illustrative and exemplary, but not exhaustive. While some of the prior expedients are simpler than the present invention and others are more complex than the present invention, no patent or other teaching known to applicant teaches or suggests structure and operation providing the full advantages of the present invention.

SUMMARY OF THE INVENTION

An infusion needle carrier is provided. It comprises a body or main portion firmly carrying an infusion needle. A support base extending laterally from the body to selectively brace the angle of insertion of the needle is provided. In the illustrative embodiments, the support base comprises a pair of laterally opposed generally flat, broad, extended wings. A control member or handle is provided, extending above the wings. The elements are all assembled to the body member. The rear end of the infusion needle is connected to conventional tubing, connectors, or other apparatus for providing the desired medical treatment by means of the needle.

The device is handled and manipulated by the user grasping the control member or handle, preferably between the thumb and another finger. One hand is sufficient to manipulate the device. The device has a set, or unsqueezed, or locked condition. In this condition, the body member (and hence the needle) and the wings are in a rigid relationship with respect to each other, and the control member is not operative to change that relationship or release it, and instead falls or is free to fall from its upstanding position to a flat out of the way position.

The device has a squeezed or depressed condition in which, when elements of the control member are squeezed together by the fingers of the operator, a camming action takes place. The camming action releases the wing members so that they are free to move angularly with respect to each other, and hence to permit adjustment of the angle of insertion of the needle into the patient. In this squeezed condition, rotational motion of the control member in a direction normal to the long dimension of the needle causes a corresponding rotation of the needle, which aids in the insertion technique. Relaxation of the squeezing action on the control member removes the camming action, and causes the device to go into the set condition.

In use, the carrier is grasped between the thumb and the finger of the operator by its control member. With one hand operation, the operator holds and guides the needle for insertion. During the insertion step, the angle between the needle and the skin of the patient may be varied by the operator. At all usual angles of insertion, the wings accomodate and stay in contact with the skin of the patient. Sideways motion of the control member at this stage results in corresponding rotation of the needle, which is a useful technique in insertion. During such rotation, the wings accomodate and retain their contact with the skin.

When insertion is achieved, squeezing pressure on the control member is relaxed. At this stage, the needle is locked against further rotation with respect to the wings. The wings are locked against further mutual angular displacement and against angular displacement with respect to the body. The wings thus act as fixed braces holding the needle at the desired angle of insertion. The control member at this stage is disengaged from affecting angular relationships, but is still physically connected to the device. It falls or may be pushed to a position just above and contiguous to the wing elements and out of the way. Manipulation of the control member as described above may be repeated, if desired, to readjust needle placement. The process is then conventional, utilizing adhesive tapes, covering materials, or any combination thereof or any other conventional affixing or infusion set maintenance expedients.

Advantages of this invention are made apparent from the foregoing description of the mode of use. For example, there is the simple one-hand manipulation, the ability to vary the angle of insertion, the ability to rotate the needle and its sharpened beveled end, and the ability to then affix, set or lock the apparatus in the desired configuration when proper insertion has been achieved. In addition, the device, in its various embodiments, is relatively simple, reliable, and elegant in its conception.

BRIEF DESCRIPTION OF THE DRAWINGS

The invention is best understood in connection with the accompanying drawings in which.

DESCRIPTION OF THE PREFERRED EMBODIMENT

FIGS. 1-7 pertain to the preferred embodiment. The invention is best initially described in connection with FIGS. 1 and 2. A hollow intravascular infusion needle 37 with a biased cut end forming an insertion point is provided. This needle is intended to be insertable below the skin of a patient, generally into a vein, artery, or the lymphatic system. It is desired to have the needle easily manipulatable, supportable at a desired angle, and capable of being fixedly maintained in the desired position.

Figure 1:
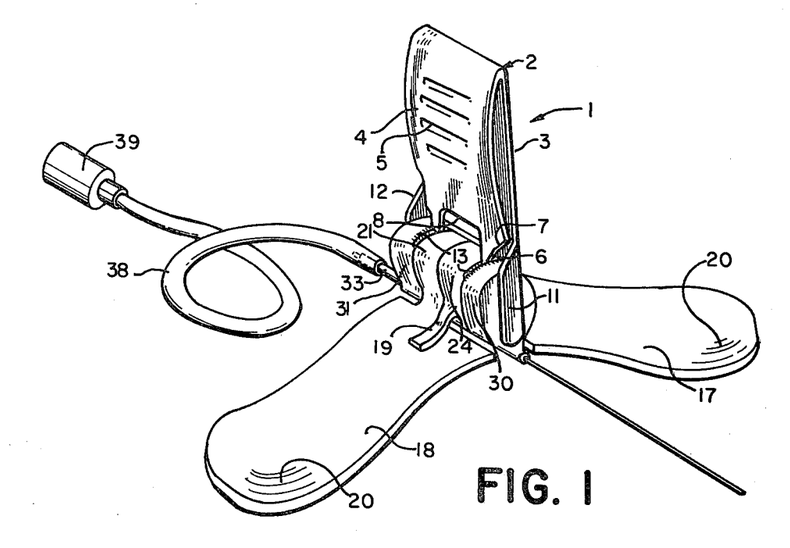
FIG. 1 is a perspective view of the preferred embodiment of the infusion needle carrier.
Figure 2:
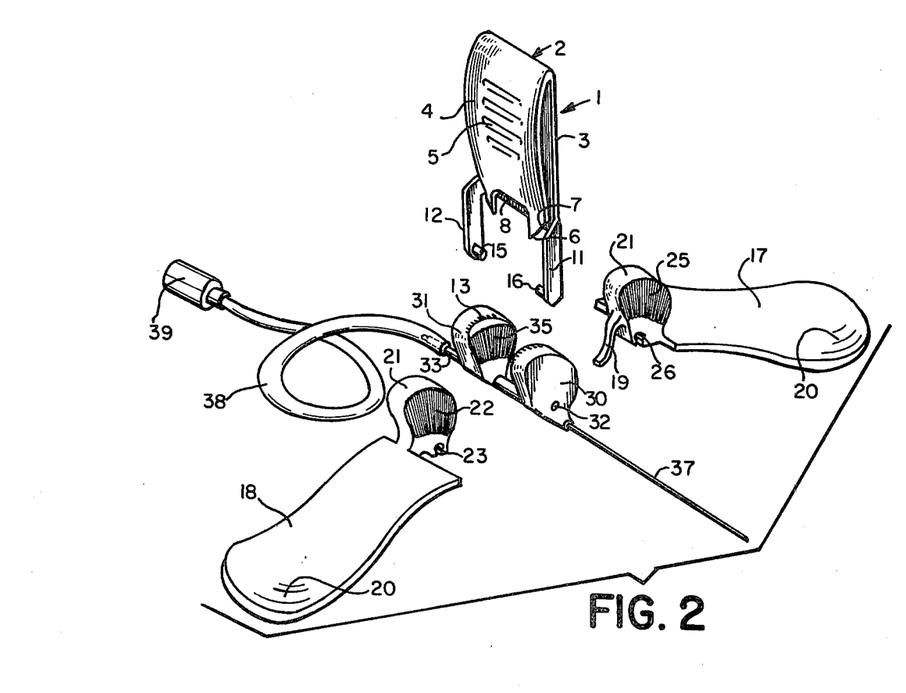
FIG. 2 is an exploded perspective view of the infusion needle carrier of FIG. 1.

The front end of the needle 37 is sharpened for insertion. The rear end of the needle is inserted into the end of a flexible tube 38, generally of plastic. The other end of tube 38 terminates in conventional connecting means, in the illustrated embodiment the female receptacle of a conventional luer lock. In accord with conventional practice, this cannula system is connected to a source of liquid desired to be infused into the patient. The structure described above is entirely conventional.

The infusion needle carrier is generally designated 1. It comprises a control member or handle generally designated 2. The control member 2 is preferably made of one integral plastic piece. It includes a flat side 3 and a generally opposed convex curved side 4. Curved side 4 is preferably provided with a plurality of identations 5, to provide a gripping surface.

At each of its side edges, the curved side is provided with an extension. Each extension is a separator. Each extension comprises a camming section or cam 6, and a stop 7. The more detailed explanation of the separators is made below in connection with FIG. 4.

The flat side 3 of control member 2 is extended at each of its edges, to a distance greater than the extensions described in connection with the curved side 4. These extensions comprise arm 11 at one side and arm 12 at the other side. Arm 11 is provided at its distal end with a pivot pin 16, and arm 12 is provided at its distal end with a pivot pin 15. The pivot pin 15 and 16 face inwardly toward each other.

A body or main or central member is provided. The body generally comprises three elements. It is generally made of one integral piece of plastic. One of the elements is a tube 33. Tube 33 is dimensioned so as to receive needle 37 firmly to resist relative rotation. The insertion or piercing end of needle 37 extends from one end of tube 33 at one end of the body. Tube 33 extends beyond the other end of the body, and needle 37 preferably extends through tube 33 and a short distance beyond the end of the extension of tube 33. Preferably, the sealing insertion into flexible tube 38 is made by the outer surface of the extension of tube 33.

The other two main elements of the body are body hinge block 30 and body hinge block 31. The major dimensions of body hinge blocks 30 and 31 extend in the same direction normal to tube 33. Each hinge block is provided with a circular contour upper surface with the circular contour being normal to the direction of tube 33. Each hinge block has an inner face opposing the inner face of the other hinge block. Each said inner faces is preferably provided at least in part with a friction area 35. The term "friction" as used herein does not necessarily or exclusively technically relate to friction phenomena, but may comprise serrations or other irregularities for a purpose described further below.

At least a portion of the upper circular contour of each hinge block 30 and 31 is preferably provided with a friction area 13. The friction area 13 is adjacent the inner edge of the upper surface. The same comments as to the meaning of "friction" in this context as described above apply here also. The further detailed structure and the operation of these elements is described further below in connection with other drawings.

Another element of the infusion needle carrier 1 comprises a pair of similar but not identical members. The last two named members together comprise a support base. The support base includes a first wing 17 and a second wing 18. The term "wing" is not intended to have any aerodynamic meaning or to itself limit the shape or appearance of the member, but is used as an apt descriptive term for one preferred form of the pair of elements comprising the support base.

The first wing 17 comprises a relatively flat, broad extended portion having a paddle or wing shaped appearance. The first wing 17 extends normal to the direction of the tube 33. In the area of the flat portion of the wing most remote from the needle and near the forward edge, the flat portion of the wing is preferably formed into a convex curve, with the convexity facing downward. The convex portion of wing 17 is designated 20. The reason for this shape is described further below.

The second wing 18 is provided with a flat extended portion also having a downward-facing convex portion 20, exactly as described in connection with the first wing.

First wing 17 includes a wing hinge block 21. As best shown in FIG. 2, wing hinge block 21, preferably integral with the flat portion, extends upwardly from the flat portion at the end of the wing closest to the tube 33. The upper surface of wing hinge block 21 is provided with a circular contour, and at least part of both the front and the rear faces of wing hinge block 21 are provided with friction areas 25. The explanation of said friction areas made above in connection with hinge blocks 30 and 31 applies in this connection also. The second wing 18 is similarly provided with a wing hinge block 21, including friction areas 22, and as to which the same description applies as applied to the wing hinge block 21 on the first wing 17.

Wing hinge block 21 on first wing 17 is provided with a hole 26 therethrough, running from front to back, at the bottom of the wing hinge block, and being slotted or opened to preferably form a keyhole structure. This hole 26 and its slot are dimensioned so as to fit over tube 33, being capable of being forced onto and over tube 33 with a snap action resulting from slight deformation of the plastic around the slotted portion, and thence receiving tube 33 through the larger circular portion of hole 26 so as to permit rotational movement between first wing 17 and the tube 33, with the resilience of the plastic resisting easy disengagement of wing 17 from tube 33.

Second wing 18 is similarly provided with a hole 23 as to which the description made above in connection with hole 26 also applies. This description of second wing 18 completes the essential aspects of that structure. The only significant difference between second wing 18 and first wing 17 is that first wing 17 has in addition to the described structure a tongue spring 19. This spring 19 is preferably integrally part of the entire first wing 17. It extends outwardly from wing hinge block 21 in a direction generally opposite to that of the flat broad wing-like portion.

The elements described above are dimensioned so that second wing 18 may be snapped into the stated position over tube 33 between hinge blocks 30 and 31, toward the rear of the available space between said two hinge blocks. Similarly, first wing 17 may have its hole 26 snapped in position over tube 33 between hinge blocks 30 and 31, but toward the front of the available space, so that in order from the front to the back, the assembly is hinge block 30, wing hinge block 21 on first wing 17, wing hinge block 21 on second wing 18, and hinge block 31. As assembled, the spring 19 lies above the surface of the flat broad extension of second wing 18, and the distal end of spring 19 lies above the surface of the flat broad extension of second wing 18, and contacts said surface. The natural elastic properties of the preferable plastic of which the body is made permit elastic deformation of the body particularly the tube, and the dimensions of the hinge blocks and said elasticity force the assembled elements into a mutually contacting condition resisting relative movement.

When assembled, the two wings 17 and 18 ride on tube 33 and are free to rotate around it under certain conditions of operation as described further below. Control member 2 is fixed to the body element by the means of pivot pin 16 being inserted into pivot hole 32 in hinge block 30, and pivot pin 15 being inserted into corresponding pivot hole 32 in hinge block 31. This last mentioned assembly, and the more detailed structure of certain portions of the device and its operation are best understood in connection with aid of FIGS. 3 and 7.

Figure 4:
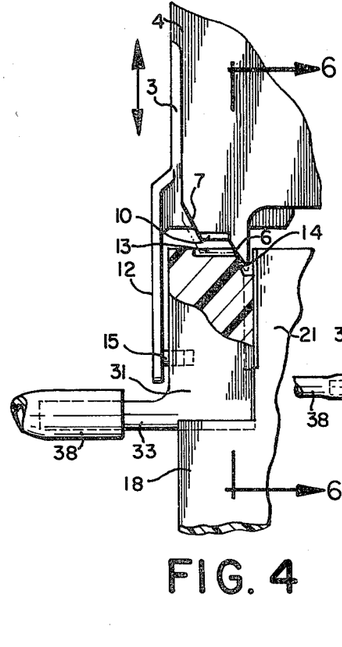
FIG. 4 is an enlarged fragmented view, partially broken away and partially in section, of a portion of a carrier shown in FIG. 3.

It is seen particularly as shown in FIG. 4, that the upper portion of the inward face of each hinge block is provided with a taper or chamfer 14. In the assembled condition, this taper 14 defines a short entrace slot between the hinge block and the wing hinge block 21. The purpose of this entrace slot or guideway is best understood in connection with the further detailed structure and operation of the control member 2. In its normal and unbiased position, the control member 2, when assembled in the complete device, is dimensioned so that the cam 6 is above and does not operatively engage the taper 14. In this condition, all the hinge blocks and wing hinge blocks are in contact with their adjacent elements, and the mutual friction areas, as have been defined, serve to keep the hinge blocks and wing hinge blocks from relative movement. As possibly most clearly shown in FIG. 7, a friction area 22 on a wing hinge block 21 is preferably a plurality of closely spaced shallow narrow serrations which may be arranged roughly radially. This type of friction area is representative of the other friction areas in the device.

It is apparent that the coaction of the friction areas as described tends to prevent relative rotation, but upon the exertion of overriding force, the mutually engaging friction areas can slip. This is intended and desired as a safety feature. However, under ordinary conditions of use, in the mutually engaged position, the entire infusion needle carrier 1 is considered locked and fixed in position, with the wings 17 and 18 being set in their angular relationship to the body portion.

Figure 3:
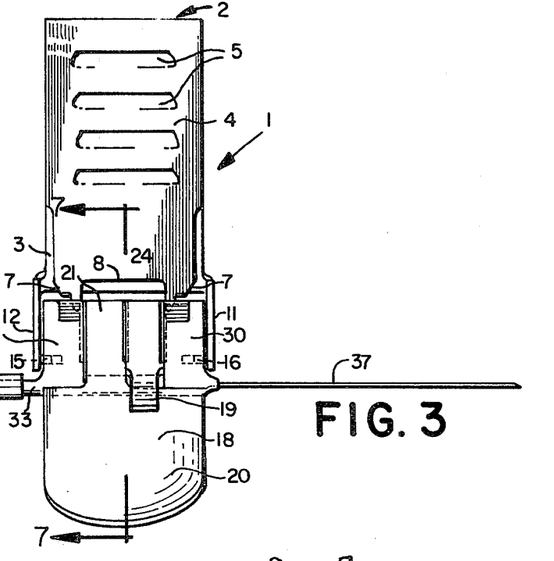
FIG. 3 is a right side elevation of the carrier of FIG. 1.
Figure 5:
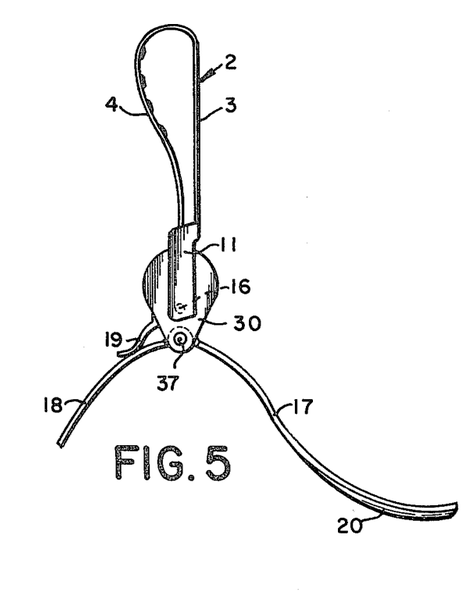
FIG. 5 is a front view of the carrier of FIG. 1, partially fragmented.
Figure 6:
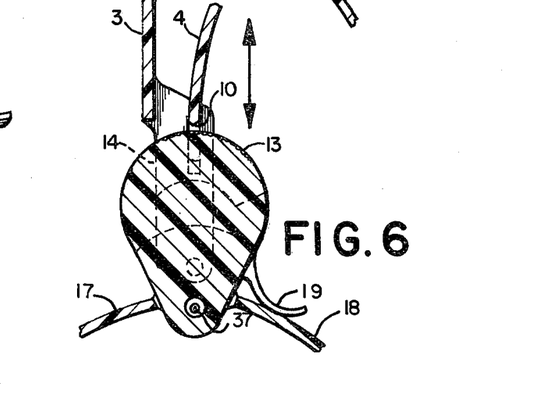
FIG. 6 is an enlarged fragmented sectional view taken on line 6—6 of FIG. 4.
Figure 7:
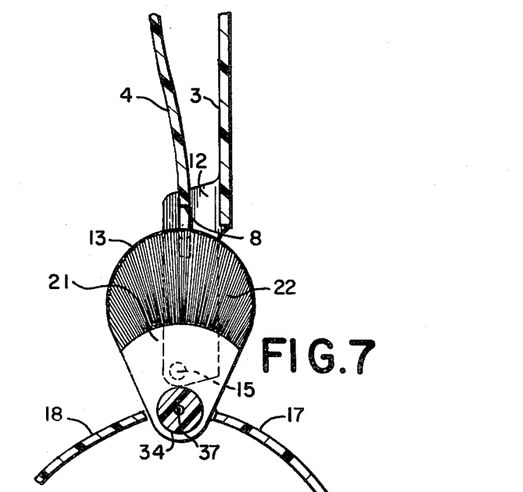
FIG. 7 is an enlarged, fragmented, sectional view taken on line 7—7 of FIG. 3.

Returning now to the structure of the handle 2, as perhaps best shown for this purpose in FIG. 5 and also FIGS. 3 and 4, it is seen that there is a space between the flat side 3 and the curved side 4. The user's fingers grasp the broad sides of the control member or handle 2. When the user squeezes his fingers together, the sides 3 and 4 are forced together, primarily by elastic deformation of the curved side 4. The effect of this deformation is to drive the cam 6 downwardly. This selective motion is indicated by the double ended arrow in FIG. 4. When the cam 6 descends, it engages the taper 14, and through a camming action, it forces the two body hinge blocks 30 and 31 away from contact with the two wing hinge blocks 21 respectively. There is enough elastic give in the elements of the structure, particularly in the elongated relatively thin tube 33, to permit this kind of small dimension deformation.

When the mutual friction areas are disengaged, the wings 17 and 18 are free to rotate with respect to the body portion.

As best shown in FIG. 4, the stop 7 on the curved side 4 is provided at its lower edge with a tooth 10. This tooth may simply be a slightly sharpened termination to the bottom of the stop. As has been described, friction areas 13 are provided on the inward upper portions of the top surface of the hinge blocks. Preferably, the friction areas 13 comprise a plurality of parallel narrow closely spaced serrations, alligned parallel to the direction of the tube 33.

It will now be appreciated that as the squeezing of handle 2 continues further, after the camming action of cam 6 has taken place, the tooth 10 of stop 7 descends and engages one of the serrations or grooves in the friction area 13. This has the effect of locking the handle rotationally with the hinge blocks 30 and 31. This condition is called the depressed condition. In this condition, the two wing portions 17 and 18 are free to rotate with respect to the hinge blocks 30 and 31, and the body portion, and the handle 2, which are locked together as a unit. To provide clearance between the cams 6, the side 4 is cut away to form a bridge 8. This is simply to prevent an unwanted contact of part of side 4 with a portion of the wing hinge blocks 21.

When the apparatus is in the depressed condition, as described, the tongue spring 19, bearing on the top surface of wing 18, and being itself secured at its proximal end to wing 17, forces the two wings downwardly. That is, if the apparatus is held free, and the handle is squeezed, the two wings swing away from a relative position approaching the horizontal and rotate downwardly toward each other. It is also apparent that due to the above described structure, if the infusion needle carrier 1 is then pressed downwardly against a surface, such as the skin of the patient, the wings 17 and 18, free to rotate relative to the body of the carrier, can swing outwardly and upwardly away from each other against the bias of spring 19.

A generally desirable contour of the wings, as seen from the front edge, is best shown in FIG. 5. There is one other significant contour aspect of the wings. Preferably, the forward, distal section of each wing is provided with a downward looking convexity at convex portion 20. The reason for this preferred structure is apparent when the context of intended use on skin is understood.

When the control member 2 is in the depressed condition, the wings are movable against the spring 19 biased as described. When manual squeezing pressure on control member 2 is released, and the stop 7 and cam 6 rise, the carrier 1 goes into the set condition. In that condition, the wings 17 and 18 are set, fixed, or locked (except for safety slippage) with the body member, including the needle 37. In the set condition however, the control member 2 is free to loosely rotate without affecting any of the other elements of the assembly. This is desirable. The control member may simply be swung or flopped out of the way to one side.

In use, the skin or other surface of the patient to be treated is suitably prepared. The infusion needle carrier is grasped by the handle 2. The thumb and one opposing finger of one hand is all that is necessary. The handle is squeezed, and the apparatus goes into the depressed condition. The wings are then in their most downward and closely mutually approaching state. The carrier is brought into contact with the surface of the patient to be treated. It is guided so that the needle 37, to be inserted subcutaneously, approaches the skin at the desired angle. As the carrier approaches the skin, the pressure of the skin forces the wings 17 and 18 upwards and away from each other as has been described. Because the needle is approaching the patient's surface at an angle, the contact with the skin is made at the convex portion 20 of the wings 17 and 18.

Forward motion of the carrier, after contact of the needle point is made, starts insertion of the needle. It is important to note that in this depressed condition during which the angle is adjustable, and the wings can move while retaining a biased contact against the skin, the control member or handle 2 is locked against mutual rotation with the body member. When it is recalled that the needle 37 is firmly affixed to the body member, it is apparent that in the depressed condition, not only can the angle be adjusted, but by rotating the handle from side to side, the needle can be rotated. This is a valuable part of the needle insertion technique. When the right amount and angle of insertion is achieved, squeezing pressure on the handle is released, and the carrier goes to the set condition. The operational sequence described above is entirely repeatable for the purpose of readjusting needle placement. As has been described above, in the set condition, the wings are locked in the selected angular position, and the control member is then free to loosely rotate. If may be dropped or swung out of the way, and the apparatus secured in a conventional means with the use of adhesive covering materials, tape, or a combination of these means or their equivalents, so that the needle may be secured in the patient's surface.

Figure 8:
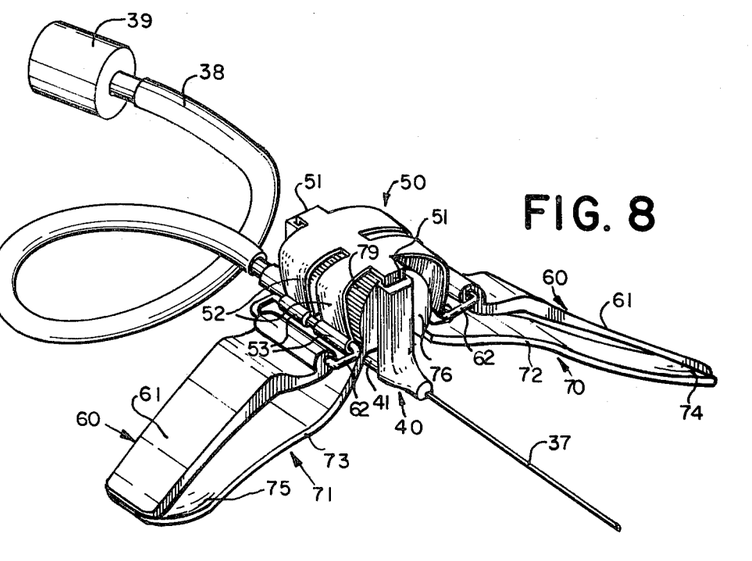
FIG. 8 is a perspective view of another embodiment of the infusion needle carrier.
Figure 9:
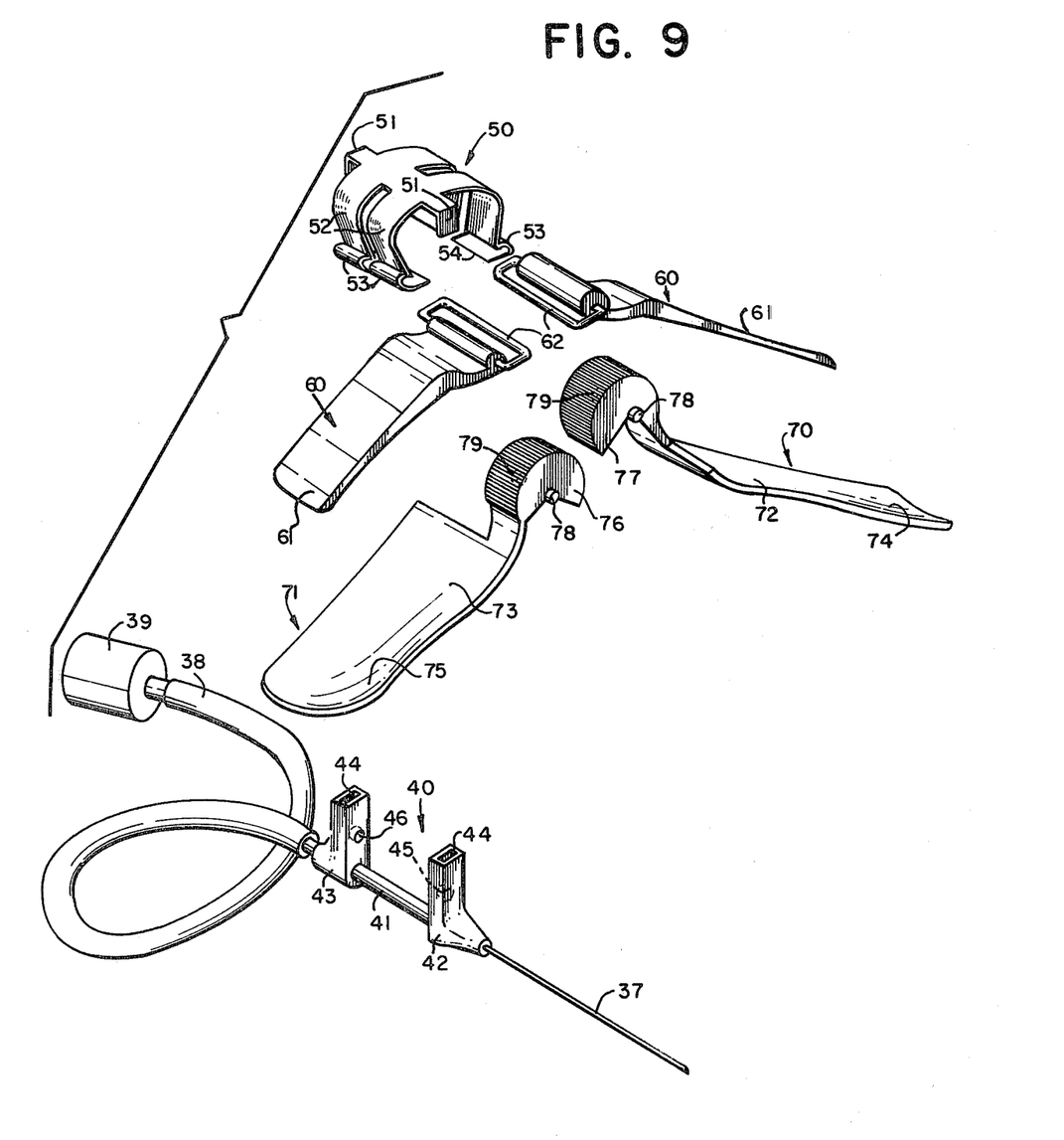
FIG. 9 is an exploded perspective view of the infusion needle carrier of FIG. 8.
Figure 10:
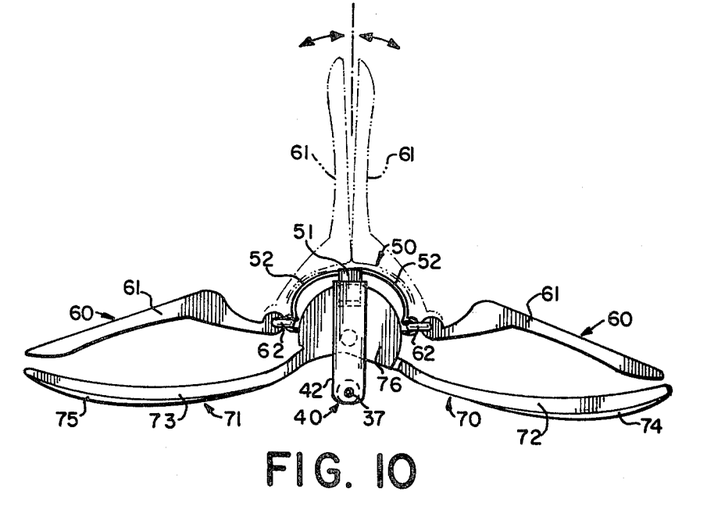
FIG. 10 is a front view of the carrier of FIG. 8.

An alternate embodiment, employing the same general concepts of structure and operation, is illustrated in FIGS. 8–10. In the description of the preferred and alternate embodiments, like reference numerals refer to like parts and are not necessarily described again.

The alternate embodiment is best initially described in connection with FIG. 9. The infusion needle carrier has the same intended function as the carrier in the preferred embodiment, and is manipulated and operates in an identical or analagous way.

A body or main or central member generally designated 40 is provided. Body member 40 includes a tube 41 through which infusion needle 37 is firmly inserted, connecting to flexible tube 38 and connector 39, as has been described above in connection with the preferred embodiment. The body member 40 also includes hinge blocks 42 and 43. The rear hinge block 43 is provided with a pivot pin 46, and the front hinge block 42 is provided with a pivot hole 45. Each of the hinge blocks 42 and 43 is provided with an upwardly facing recess 44.

A pair of wings, first wing generally designated 70 and second wing generally designated 71 are provided. First wing 70 has a first position 72 and second wing 71 has such a flat portion 73. The forward distal sections of both wings 70 and 71 are provided with downward facing convex portions 74 and 75 respectively. The flat broad portions and the convex portions are the same as have been described above in connection with the preferred embodiment, and a detailed recitation of the structure and its function and purpose is not repeated. First wing 70 is provided with a wing hinge block 77 and a second wing 71 is provided with a wing hinge block 76. As shown, the upper surfaces of these wing hinge blocks are contoured into a curved, preferably circular contour normal to the direction of tube 41. The upper surfaces comprise a friction area as that term has been defined and described above.

The front looking faces of the wing hinge blocks 77 and 76 are provided with pivot pins 78. The rearward looking faces of the hinge blocks 77 and 76 are provided with pivot holes 79. When assembled, the order of the elements is the front hinge block 42, the first wing hinge block 77, the second wing hinge block 76, and the rear hinge block 43. The body 40 is slightly sprung or deformed, due to the inherent elastic properties of the elongated tube so that the appropriate respective pivot pins fit into the apropriate respective pivot holes to permit retention and relative rotation. It is of course understood that it is only necessary to provide pivot means between the elements described above. The particular arrangement and order of pivot pins and pivot holes as described and shown is merely illustrative. For example, it is apparent that the male and female pivot means on different elements could be interchanged for construction or assembly purposes. A handle or control member generally designated 60 is provided. The control member 60 is in two identical parts. Each part includes a flat grasping portion 61. At the innermost ends of each element of the control member 60 is a lever ring or camming ring 62. This is a horizontally oriented loop, preferably of metal. Alternatively, the grasping portion 61 and camming ring 62 of each part of control member 60 may be constructed as a single integral unit of metal or of a molded plastic of sufficient tensile strength. The lever rings or camming rings 62, together with associated structure to be described, together comprise locking-unlocking means, as does the cam and stop structure and its associated elements in the preferred embodiment.

A spring clamp generally designated 50 is provided. The spring clamp 50 is a generally arctuate piece of spring metal. It comprises a pair of downwardly extending studs 51, as shown. Each of these studs 51 fits into a respective recess 44 in a hinge block of the body member. The fit is a force fit so that once the assembly is made, it will remain assembled under ordinary conditions. It is to be understood that the above described means for affixing the front and rear portions of spring clamp 50 to the respective body hinge blocks is a matter of manufacturing preference and, for example, such means may be alternatively accomplished by or augmented with the use of cement material or by shaping the studs 51 to grip exterior portions of the body hinge blocks.

The spring clip 50 also includes two opposed sets of pairs of downwardly depending legs 52. Thus, there are preferably four downwardly depending legs in all. The bottom of each leg 52 is bellied outwardly into a curve 53 and ends in an inwardly facing tooth 54.

The infusion needle carrier alternate embodiment is assembled as best shown in FIGS. 8 and 10. The inner portions of the lever rings or camming rings 62 are seated in the concavity of the spring clip curves 53, and the studs 51 are forced into the recesses 44. It is apparent that the provisions of a pair of legs 52 on each side is a matter of engineering choice, and that functionally a single leg 52 on each side could be used.

The arctuate shape of spring clamp 50 is such that when the needle carrier is assembled, the legs 52 are elastically forced outwardly away from each other, so that there is an inward spring bias. This bias provides a reliable retention function for the camming rings 62, and also causes the teeth 54 to press inward against and engage the friction areas on the upper surface of the wing hinge blocks 76 and 77.

When the carrier is free-standing, that is, is not being manipulated or controlled, each part of the control member 60 extends or lies in the general position indicated in FIG. 10, that is, in a downward position, with the ends thereof remote from each other, and substantially flat and contiguous with the upper surfaces of the wings 70 and 71. This is the functional equivalent of the unsqueezed or set condition of the carrier as has been described in connection with the preferred embodiment. That is, when no squeezing action is applied to the handle or control 60, the carrier is set, with the wings 70 and 71 being locked against relative rotation with respect to the body 40.

When each of the two parts of the control member 60 are squeezed together, by being rotated upwardly so that they approach each other as shown in the phantom line rendering in FIG. 10, the camming rings 62 bear outwardly on the spring clamp or clip curves 53 and disengage said teeth 54 from the surface of the wing hinge blocks. As is clearly shown in FIG. 10, the preferable shape and dimension of the control member 60 is such that as the two parts are brought together to the condition shown in the phantom lines, they touch centrally just above the mid-point of the carrier or, alternatively, they each bear on the upper central portion of the spring clamp 50, and continued squeezing pressure produces a lever action around the fulcrum thus produced which serves to withdraw the teeth 54. This is the equivalent of the squeezed or depressed condition as described in connection with the preferred embodiment. In this condition, the wing hinge blocks 76 and 77, and consequently the first and second wings 70 and 71 are free to rotate relative to the body member 40. In this condition, as has been described above in connection with the preferred embodiment, the relative angular disposition of the wings is variable, to accomodate the preferred angle of insertion of the needle 37 into the patient. At the same time, when the parts of the control member are squeezed together as shown in the phantom lines in FIG. 10, there is a rigid continuous connection from the control member to the body, and hence to the firmly held needle 37, by the way of the studs 51 in their recesses 44. Thus, the needle 37 may be rotated by rotating the control member 60. This is functionally equivalent to the preferred embodiment.

When the squeezing action on handle parts 60 is released, they return toward their solid line representation as shown in FIG. 10, the teeth 54 at the ends of curves 53, engage the wing hinge blocks and lock the wings from further angular variation (except for overriding slippage as a safety factor). At this point, the control member 60 is in the equivalent of a condition of being flopped out of the way to one side in the first embodiment. The affixation of the needle carrier to the patient may then proceed in the conventional manner as has been described.

Except for those portions preferably made of metal or spring metal, it is preferred to make the parts of the carriers, in all embodiments, out of molded plastic. The dimensional range of the carriers is established by comparison with conventional infusion needles. The plastic is in itself not critical, but may for example be one of the common molded structural plastics such as polypropylene or polystyrene with the choice and the manufacturing techniques depending on well known design considerations. It is theoretically possible to rely on the natural friction of engaged surfaces where friction areas are described. However, it is preferable to roughen or otherwise treat the surface to make the desired engagement characteristics more secure. In particular, the provision of grooves or serrations to constitute these areas, arranged as indicated in the drawings, is desirable.

As has been described, some advantages of this carrier are the ability for the operator, by using one hand, to firmly grasp and guide the needle, to choose a location and angle of insertion, to control the rotational setting of the needle, and to automatically provide rigid braces to hold the needle at the desired angle of insertion. It is also advantageous in that by simple release of squeezing pressure when the desired insertion is achieved, the carrier has been set to hold the needle firmly in the desired angle of insertion, and the final affixation by taping or otherwise can proceed. The relatively flat conformation of the carrier once the control member is swung to its resting position is also advantageous. It is understood that normally the carrier would be disposable after a single use. It is appreciated that the simplicity and use of operation is clinically desirable. The invention has particular, but not exclusive, application to pediatric medicine.

Although illustrative embodiments of the invention have been shown and described, it is to be understood that various modifications and substitutions may be made by those skilled in the art without departing from the novel spirit and scope of the present invention.

I claim:

1. An infusion needle carrier comprising:
   a body member, said body member including at least one body hinge block means;
   an infusion needle firmly affixed to said body member;
   a laterally extending support base portion affixed to said body member for selective movement with respect to said body member;
   a control member affixed to said body member, said control member having two opposed sides and having a manually squeezed condition in which said opposed sides are forced towards each other and an unsqueezed condition;
   camming means on said control member, said camming means being selectively operatively associated with said support base portion, the engagement condition of said camming means being operatively responsive to said squeezed and unsqueezed conditions of said control member;
   whereby, when said control member is in said squeezed condition, said camming means are adapted to release said body member and said support base portion from mutual locked engagement thereby disposing them in an unset non-locked condition with respect to each other, and, when said control member is in said unsqueezed condition, said support base portion and said body member are in a set locked condition with respect to each other, said engagement condition of said camming means thereby determining said set and unset condition.

2. An infusion needle carrier as set forth in claim 1 wherein said control member includes means to selectively rigidly lock said control member to said body member, said control member and said body member being rigidly locked only when said control member is in said squeezed condition.

3. An infusion needle carrier as set forth in claim 2 wherein said body member includes a tubular element firmly engaging said infusion needle, said support base portion comprises two laterally extending wing members, said wing members each including a wing hinge block means, each said wing hinge block means being disposed for selective rotation about said tubular element.

4. An infusion needle carrier as set forth in claim 3 wherein said control member includes at least one tooth element, each said tooth element being operatively connected for movement with said camming means, and each said tooth element being selectively engageable with each said body hinge block means.

5. An infusion needle carrier as set forth in claim 4 wherein at least part of the surfaces of some of said body hinge block means and said wing hinge block means are provided with friction areas, each of said friction areas being selectively operatively engageable with a tooth element, a camming means, or an opposed friction area, whereby rigid engagement and locked set engagement is further secured.

6. An infusion needle carrier as set forth in claim 5 wherein at least some of said friction areas comprise a plurality of closely spaced shallow serrations.

7. An infusion needle carrier as set forth in claim 6 wherein said body member includes two said body hinge block means, spaced apart, and said tubular element extends between said body hinge block means, each of said wing hinge block means being positioned on and around said tubular element, between said body hinge block means.

8. An infusion needle carrier as set forth in claim 7 wherein each of said wing members has said wing hinge block means at its proximal end, and the distal end of said wing members, at the forward edge thereof, is provided with a downward facing convex portion.

9. An infusion needle carrier as set forth in claim 3 wherein said body member is provided with two said body hinge block means, and said tubular element is disposed between said body hinge block means, and
   said control member is pivotly connected for free relative rotation to said body hinge block means, and
   each of said wing hinge block means is disposed at the proximal end of each of said wing members, both of said wing hinge block means being disposed between said body hinge block means thereby forming a junction between each said wing hinge block means and the body hinge block means adjacent thereto.

10. An infusion needle carrier as set forth in claim 9 wherein said control member is provided with a pair of said camming means, each of said camming means being downwardly dependent and being positioned above the junction between one of said body hinge block means and one of said wing hinge block means, and
    at least one of said two opposed sides of said control member being a convex curved side, and said camming means being affixed at the lower edge of said curved side, whereby when said curved side is squeezed it deforms and forces said camming means to a depressed condition, each said camming means entering said junction between one of said wing hinge block means and one of said body hinge block means, and bearing against one of said body hinge block means, said camming action forcing said body hinge block means out of contact with said wing hinge block means.

11. An infusion needle carrier as set forth in claim 10 wherein said control member is provided with a stop means near each of said camming means, each said stop means including a said tooth element, each of said stop means being positioned above one of said body hinge block means, and said stop means being operatively connected to said camming means so as to lower into a depressed condition with said camming means, each of said stop means contacting the upper surface of one of said body hinge block means when in the lowest extreme depressed condition.

12. An infusion needle carrier as set forth in claim 11 wherein each of said body hinge block means is provided with a taper at the inward edge thereof adjacent to the upper edge of the closest said wing hinge block means, whereby a guideway is provided for the insertion of said camming means, and said camming means is so positioned that in the depressed condition, said camming means contacts said taper.

13. An infusion needle carrier as set forth in claim 12 wherein each of said wing hinge block means has a pair of side faces, and each of said body hinge block means has at least an inner face, and each of said faces on said wing hinge block means and said body hinge block means are provided with friction areas, and
    each of said body hinge block means has an upper surface, and at least part of each said upper surface of said body hinge block means is provided with a friction area, each of said upper surface friction areas being positioned to be contacted by said stop means on said control member, when said stop means are in said extreme depressed condition.

14. An infusion needle carrier as set forth in claim 13 wherein said friction areas comprise a plurality of closely spaced shallow serrations, said serrations on the opposing said faces of said wing hinge block means and said body hinge block means being adapted to mesh and interlock when said block means are in contact, and said serrations on each said upper surface being adapted to receive and interlock with a said tooth element, when engaged with a said tooth element.

15. An infusion needle carrier as set forth in claim 14 wherein a spring means is provided between said wing members, said spring means biasing each of said wing members toward a downward position.

16. An infusion needle carrier as set forth in claim 3 wherein said body member includes a tubular element firmly engaging said infusion needle, and said body member includes two said body hinge block means, with at least part of said tubular element disposed between said body hinge block means, and
    each of said wing hinge block means is disposed at the proximal end of each of said wing members, said wing members being affixed to said body member with said wing hinge block means adjacent to each other, and each of said wing hinge block means positioned between said body hinge block means, and
    pivot means provided on each of said body hinge block means and each of said wing hinge block means, said pivot means coacting with each other, to align and retain said wing members for rotation relative to each other and relative to each said body hinge block means.

17. An infusion needle carrier as set forth in claim 16 wherein said camming means includes a camming ring at the proximal end of said control member opposed sides.

18. An infusion needle carrier as set forth in claim 17 wherein a spring clamp means is provided at least partly above and around said wing hinge block means, said spring clamp means being provided with at least one tooth element at a lower end thereof, each said tooth element being engaged to and movable in response to said camming ring and, being selectively engageable with said wing hinge block means.

19. An infusion needle carrier as set forth in claim 18 wherein said means to selectively rigidly lock said control member to said body member comprises at least one downwardly extending stud member on said spring clamp means, each said stud member being firmly affixed to said body hinge block means.

20. An infusion needle carrier as set forth in claim 19 wherein each of said wing hinge block means has an upper surface, each said surface being curved, and each said surface being provided with a plurality of closely spaced shallow serrations, adapted to be selectively engageable with a said tooth element.

21. An infusion needle carrier as set forth in claim 20 wherein said spring clamp means is provided with a plurality of downwardly depending leg members, and each of said leg members terminates in an outwardly bellied portion, and each of said outwardly bellied portions terminates in a said tooth element.

* * * * *